United States Patent [19]

Harris

[11] Patent Number: 5,087,691
[45] Date of Patent: Feb. 11, 1992

[54] POLY-PHENYLATED DIAMINES AND THEIR USE AS POLYCONDENSATION MONOMERS IN THE SYNTHESIS OF POLYAMIDE, POLY(AMIDE-IMIDE), AND POLYIMIDE POLYMERS

[75] Inventor: Frank W. Harris, Akron, Ohio

[73] Assignee: University of Akron, Akron, Ohio

[21] Appl. No.: 402,272

[22] Filed: Sep. 1, 1989

[51] Int. Cl.$^5$ .............................................. C08G 69/26
[52] U.S. Cl. ...................................... 528/353; 528/347; 528/348; 528/350
[58] Field of Search ................. 528/347, 348, 350, 353

[56] References Cited

U.S. PATENT DOCUMENTS 4,239,880 12/1980 Darms .................................. 564/430
4,485,140 11/1984 Gannatt et al. ...................... 428/269

OTHER PUBLICATIONS

Harris et al., "Soluble Aromatic Polyimides Derived from New Phenylated Diamines", Poly. Mater. Sci. 60, 187-91 (1989).

Primary Examiner—Harold D. Anderson
Assistant Examiner—T. Mosley
Attorney, Agent, or Firm—Oldham & Oldham Company

[57] ABSTRACT

New polyphenylated polynuclear aromatic diamines, such as 1,3-bis[4-aminophenyl]-2,3,5-triphenylbenzene, a process for their manufacture and their use as polycondensation components for the manufacture of polyamide, polyamide-imide and polyimide polymers are described. The polymers obtained with the aromatic diamines according to the invention are readily soluble, rigid-rod polymers and are distinguished by outstanding modulus, tensile compression strength, energy absorption, coefficient of expansion and electrical properties.

15 Claims, No Drawings

POLY-PHENYLATED DIAMINES AND THEIR USE AS POLYCONDENSATION MONOMERS IN THE SYNTHESIS OF POLYAMIDE, POLY(AMIDE-IMIDE), AND POLYIMIDE POLYMERS

This invention was made with Government support under contract NAG-1-448 awarded by NASA. The Government has certain rights in this invention.

TECHNICAL FIELD OF THE INVENTION

The present invention relates to new poly phenylated aromatic diamines, a process for their manufacture and their use as polycondensation components for the manufacture of polyamide, polyamide-imide and polyimide polymers.

BACKGROUND OF THE INVENTION

Generally, aromatic polyamides, polyamide-imides and polyimides are difficult to process and generally have low solubility. Some improvement in solubility has been achieved by preparing the polymers from bulky diamines or from dianhydrides containing 3 or more aromatic rings. (compare, for example, DT-AS No. 1,595,733 and DT-OS Nos. 2,009,739, 2,153,829, 2,257,996 and 2,321,513). However, these polymers either cannot be processed from the melt, or are difficult to process from the melt and, in some cases, have inadequate heat and/or chemical stability.

More recently Darms in U.S. Pat. No. 4,239,880 has disclosed polyamides, polyamide-imide and polyimide polymers prepared from exotic poly nuclear aromatic diamines. Although the polymers manufactured using Darm's diamines show improved solubility, these polymers do not form rigid rod polymers.

It, thus, appears desirable to produce polyamides, polyamide-imides and polyimides based on poly-phenylated diamines according to the present invention which would form soluble rigid-rod polymers having outstanding modulus, tensile and compression strength, excellent energy absorption characteristics, very low coefficient of expansion, excellent thermal stability, non-conduction, excellent film processability and relatively less expense that existing polymers. These properties will make the polymers ideally suited for use in the production of antiballistics, reinforced molecular composites, microelectronic coatings and gas, liquid and solid membrane separation applications.

DESCRIPTION OF THE INVENTION

It is an object of this invention to provide novel rigid-rod, high modulus, soluble poly-phenylated polyamides, polyamide-imides, polyimides, polyamide-amide-acids, polyamide-acids based on poly-phenylated 1,4-bis(phenyl)benzene diamines where the poly phenylation is at the center benzene ring.

A further aspect of this invention is to provide novel copolymers comprising repeat units based on the new poly-phenylated diamines and one or more polycarboxylic acids, acid chlorides, esters, and other carboxylic acid derivatives and repeat units based on one or more other organic diamine(s) and one or more polycarboxylic acids, acid chlorides, esters, and other carboxylic acid derivatives where the polycarboxylic is intended to connote organic species with two or more carboxylic functions, preferentially where the polycarboxylic organic species has from 2 to 4 carboxylic functional groups.

A still further object of this invention is to provide a novel class of polyphenylated diamines and a novel class of polyphenylated dinitro organic compounds and a process for the manufacturing of these to new classes of compounds.

The new diamines of the present invention are shown in formula (I) below:

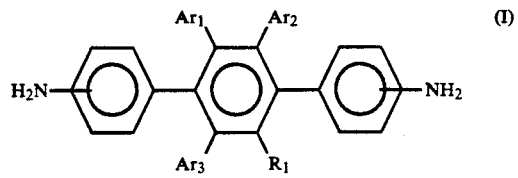

where both amino ($NH_2$) groups are independently in either the meta or para position with respect to the covalent bond to the center polysubstituted benzene ring, where $Ar_1$, $Ar_2$, and $Ar_3$ are separately and independently aryl groups selected from the representative and illustrative group consisting of a phenyl group, a halogen substituted phenyl group where halogen is meant to include F, Cl, Br and I, an alkoxy substituted phenyl group where the alkoxy substituent preferably has from about 1 to 4 carbons, a halo-alkyl substituted phenyl group where the alkyl substituent preferably has from about 1 to 4 carbon atoms, an alkyl substituted phenyl group where the alkyl substituent preferably has from about 1 and 12 carbon atoms, or an cycloalkyl substituted phenyl group where the cycloalkyl substituent preferably has from about 1 and 12 carbon atoms and where $R_1$ is selected from the representative and illustrative group consisting of a H atom, an alkyl group, cycloalkyl group or an aryl group with a H and a phenyl being particularly preferred.

The new diamines of the formula (I) can be manufactured according to the following scheme:

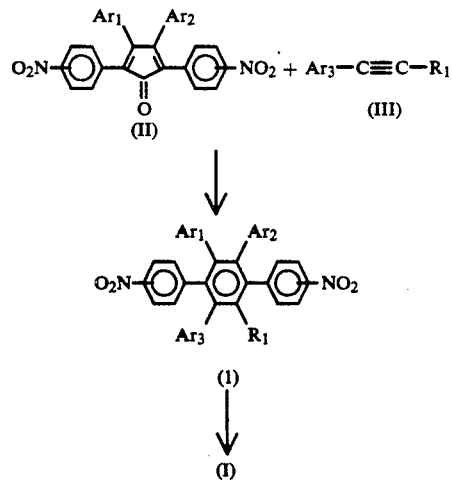

where both nitro ($NO_2$) groups in formula (II) and intermediate (1) are independently in either the meta or para position with respect to the covalent bond to the center polysubstituted benzene ring, where $Ar_1$, $Ar_2$, $Ar_3$ and $R_1$ are as previously defined. Where intermediates of formula (1) are novel dinitro compounds.

When $Ar_1$, $Ar_2$, and $Ar_3$ are all three phenyl and $R_1$ is a hydrogen atom, then the above generic synthetic scheme describes the synthesis of 1,4-bis-]4-aminophenyl]-2,3,5-triphenylbenzene, a diamine of formula (I), where 2,5-bis[4-nitrophenyl]-3,4-diphenylcyclopendienone is the corresponding compound of formula (II) and phenylacetylene is the corresponding compound of formula (III). Thus for $Ar_1$, $Ar_2$, and $Ar_3$ are all three phenyl and $R_1$ is a hydrogen atom, 2,5-bis[4-nitrophenyl]-3,4-diphenylcyclopendienone is reacted with phenylacetylene in an appropriate solvent to form 1,4-bis-[4-nitrophenyl]-2,3,5-triphenylbenzene, the corresponding intermediate of formula (1). Dinitro intermediate (I) is converted into the desired diamine 1,4-bis-[4-aminophenyl]-2,3,5-triphenylbenzene, a diamine of formula (I), by chemical reduction.

The compounds of the formula (II) and (III) are preferably employed in stoichiometric amounts. However, the reaction can also be carried out with a slight excess of one or the other reactant.

Chemical hydrogenation of intermediate (1) can be performed using well known hydrogenation agent such as iron or tin in an acid medium including ferrous sulphate, $CaCl_2$ or sodium hydrogen sulphate, titanium dichloride and/or tetrachloride in the presence of HCl, zinc in an acid or neutral medium, optionally with the addition of neutral salts, including $CaCl_2$ and $NH_4Cl$, lithium aluminum hydride, hydrazines, including hydrazine hydrate and phenylhydrazine, if necessary with the addition of Raney nickel catalysts, and sodium dithionite ($Na_2S_2O_4$) All the above reduction system are well known in the literature.

Catalytic hydrogenation can also be used employing suitable commercial catalysts in the presence of hydrogen such as palladium, palladium-on-charcoal, platinum, platinum black, platinum oxide and, above all, Raney nickel. The catalytic reduction is appropriately carried out in a suitable inert organic solvent, such as dioxane or methylcellulose.

The compounds of the formulas (II) and (III) are known or can be manufactured easily in a manner which is in itself known.

The diamines of this invention can be used as polycondensation components for the manufacturing of homopolymers and copolymers of novel polyphenylated polyamides, polyamide-amide-acids or polyamide-acids by reacting the diamines of formula (I) with one or more polycarboxylate of formula (IV)

$$Z(COY)_k$$ (IV)

where Z is an organic radical selected from the group consisting of an aliphatic radical, a cyclo-aliphatic radical, a carbocyclic-aromatic radical, or a hetero-cyclic aromatic radical, where Y is a halogen atom, a hydroxy group, an unsubstituted or substituted phenoxy group or an alkoxy group preferably having from about 1 to 18 carbon atoms, and particularly preferred having from about 1 to 12 carbon atoms, where $k$ is a whole number having a numeric value of 2, 3 or 4 and where each COY is bonded to a different atom of Z and when $k$ is equal to 3 and Z is a cyclic organic radical, then two of the COY groups are in an ortho orientation relative to each other and when $k$ is equal to 4 and Z is a cyclic organic radical, then each pair of COY groups are arranged in an ortho orientation relative to one another and one or more diamine of formula (V)

$$H_2N-Q-NH_2$$ (V)

where Q is a divalent organic radical selected from the representative and illustrative group consisting of an aliphatic radical having at least 2 carbon atoms, a carbocyclic aliphatic radical, a carbocyclic aromatic radical, or a heterocyclic radical. The resulting polymers comprise from about 1 to 100 mole percent of a repeat unit formula (VI):

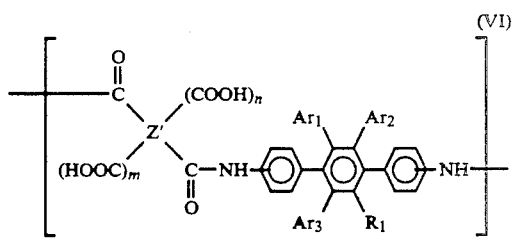

and from about 99 to 0 mole percent of a repeat unit of formula (VII)

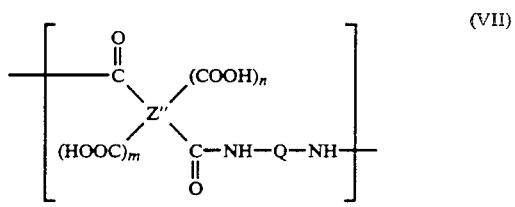

where $Ar_1$, $Ar_2$, $Ar_3$ and $R_1$ are as previously defined, n and m are whole numbers separately and independently having the numeric value of either 0 or 1 and the sum of $m$ and $n$ must be equal to $k$ minus 2 where 2 represents the number of sites involved in reaction with a diamine of formula (I) or a diamine of formula (V), Z' and Z" is separately and independently an organic radical selected from the group defining Z of formula (IV) above and Q is one or more divalent organic radical as previously defined for diamines of formula (V). When the $k$ of formula (IV) is equal to 3, then either $_m$ or $_n$ of formulas (VI) and (VII) is equal to 1 (the other is equal to 0), and the resulting polymers and copolymers are called polyamide-amide-acids. When $k$ of formula (IV) is equal to 4, then both $_m$ or $_n$ of formulas (VI) and (VII) are equal to 1 and the corresponding polymer and copolymers are called polyamide-acids.

Polyamide-amide-acids comprising 1 to 100 mole percent of repeat units of formula (VI) and 99 to 0 mole percent of repeat units of formula (VII) can be cyclized into polyamide-imides which have 1 to 100 mole percent of repeat units of formula (VIII) shown below:

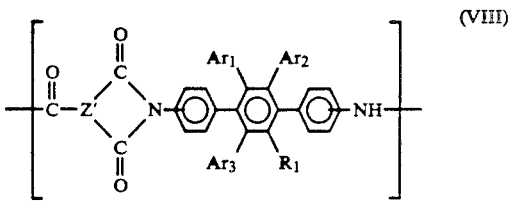

and from about 99 to 0 mole percent of a repeat unit of formula (IX)

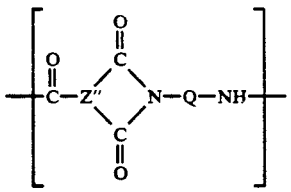

(IX)

where $Ar_1$, $Ar_2$, $Ar_3$ and $R_1$ are as previously defined and where $Z'$ and $Z''$ are separately and independently selected form the group of compound defining Z of formula (IV) above when $k$ is equal to the numeric value of 3 and Z is restricted to cyclic radicals and where Q is a previously defined.

Polyamide-acids comprising 1 to 100 mole percent of repeat units of formula (VI) and 99 to 0 mole percent of repeat units of formula (VII) can be cyclized into polyimides which have 1 to 100 mole percent of repeat units of formula (X) shown below:

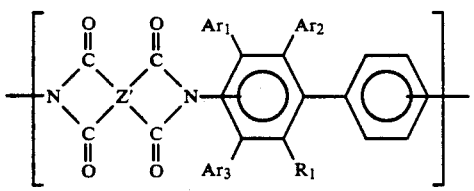

(X)

and from about 99 to 0 percent of a repeat unit of formula (XI)

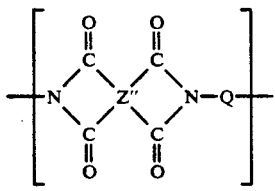

(XI)

where $Ar_1$, $Ar_2$, $Ar_3$ and $R_1$ are as previously defined and where $Z'$ and $Z''$ are separately and independently selected form the group of compound defining Z of formula (IV) above when $k$ is equal to the numeric value of 4 and Z is restricted to cyclic radicals and where Q is a previously defined.

The polymers and copolymers of the present invention are intended to include all manners of copolymers incorporating at least 1 mole percent of repeat units of formula (VI). Since the repeat units of formula (VI) can include one or more polycarboxy compounds of formula (IV), the resulting polymers can include portions that are polyamide, polyamide-amide-acids and polyamide-acids or any combination thereof. Thus, cyclization of copolymers that contain various amounts of polyamide-amide-acids and polyamide-acids can be achieved by standard chemical cyclization procedure well known in the literature.

In preparing the above polymers, a mixture of diamines of formulas (I) and (V) are reacted with a mixture of one or more polycarboxy compounds of formula (IV). The amount of diamine and polycarboxy compound should be close to a one to one molar mixture. However, 10% excess of either component is acceptable. Once the polymerization has completed, the last component to react will determine the polymer end group. The polymer end groups can, thus, be an amino group, a carboxy group or a mixture thereof. Alternately, a chain termination reagent can be added to the polymerization to force termination of the growing polymer. Such chain termination reagents are used to limit the molecular weight of the polymer and are well known in the art. Amine termination reagents commonly employed include aniline or substituted anilines. Common carboxy terminating reagents include benzoic acid or phthalic acid or their acid derivatives such as esters, acid chloride or similar acid derivatives.

The above polymerization reaction which yields polyamides and copolyamides of the present invention can be optionally carried out in the presence of a promoter such as lithium chloride or lithium carbonate. These lithium reagents are dissolved in the polymerization solvent in amounts approximately equal to the amount of amide linkages to be formed during the polymerization or in amounts approximately equal to twice the amount of diamine added.

When $k$ is equal to 2, polycarboxy compounds of formula (IV) are selected from the representative and illustrative group consisting of: malonic acid, dimethylmalonic acid, succinic acid, glutaric acid, adipic acid, suberic acid, sebacic acid and dodecanedicarboxylic acid, 1,3-cyclopentane-dicarboxylic acid, hexahydroisophthalic acid, hexahydroterephthalic acid, terephthalic acid, isophthalic acid, 4,4'-dicarboxydiphenylethane, naphthalene-2,6-dicarboxylic acid, thiophene-2,5-dicarboxylic acid and pyridine-2,3-dicarboxylic acid as well as the corresponding dichlorides and diesters according to the definition.

When $k$ is equal to 3, polycarboxy compounds of formula (IV) are selected from the representative and illustrative group consisting of: trimellitic acid 1,2-anhydride-chloride (1,3-dioxo-benzo[c]oxalane-5-carboxylic acid chloride), trimellitic acid anhydride and trimellitic acid as well as esters and anhydrides according to the definition.

When $k$ is equal to 4, polycarboxy compounds of formula (IV) are selected from the representative and illustrative group consisting of: pyromellitic acid dianhydride, 3,6-diphenylpyromellitic dianhydride, 3,3',4,4'-benzophenonetetracarboxylic acid dianhydride, 2,3,3',4'-benzophenonetetracarboxylic acid dianhydride, 2,2',3,3'-benzophenonetetracarboxylic acid dianhydride, 3,3',4,4'-diphenyl-tetracarboxylic acid dianhydride, bis-(2,3-dicarboxyphenyl)-methane dianhydride, bis(2,5,6-trifluoro-3,4-dicarboxyphenyl)methane dianhydride, 2,2-bis-(2,3-dicarboxyphenyl)-propane dianhydride, bis(3,4-dicarboxyphenyl) ether dianhydride, bis-(3,4-dicarboxyphenyl)-sulphone dianhydride, N,N-(3,4-dicarboxyphenyl)-N-methylamine dianhydride, bis(3,4-dicarboxyphenyl)-diethylsilane dianhydride, 2,3,6,7- and 1,2,5,6-naphthalene-tetracarboxylic acid dianhydride, 2,6-dichloronaphthalene-1,4,5,8-tetracarboxylic acid dianhydride, thiophene-2,3,4,5-tetracarboxylic acid dianhydride, pyrazine-2,3,5,6-tetracarboxylic acid dianhydride and pyridine-2,3,5,6-tetracarboxylic acid dianhydride as well as esters or anhydrides of the above listed compounds.

When Y of formula (IV) represents a substituted phenoxy group, then the substituents are selected from the group consisting of nitro, chlorine, fluorine, alkyl having 1 to 2 carbon atoms or alkoxy having 1 to 2 carbon and preferably selected from the group consisting of 2-, 3- or 4-nitrophenoxy group, 2,4- or 3,5-dinitrophenoxy group or 3,5-dichlorophenoxy groups or the pentachlorophenoxy, 2-methylphenoxy or 2-methoxyphenoxy group. When Y represents an alkoxy group, then the group is selected from the group consisting of methoxy, ethoxy, n-propoxy, isopropoxy, n-butoxy, tert-butoxy, hexyloxy, octoxy, decyloxy, dodecyloxy, tetradecyloxy and octadecyloxy group and preferably selected from the group consisting of methoxy, ethoxy, n-propoxy, isopropoxy, n-butoxy, and tert-butoxy.

Diamines of formula (V) are selected from the representative and illustrative groups consisting of: aliphatic diamines such as, but not limited to, di-methylenediamine, tri-methylenediamine, tetra-methylenediamine, hexa-methylenediamine, hepta-methylenediamine, octamethylenediamine and deca-methylenediamine, 2,2-dimethylpropylenediamine, 2,5-dimethyl hexamethylenediamine, 4,4-dimethylheptamethylenediamine, 3-methylheptamethylenediamine, 3-methoxyhexamethylenediamine, 2,11-diminododecane, 2,2,4- and 2,4,4-trimethylhexamethylenediamine, 1,2-bis-(3-aminopropoxy)ethane, N,N'-dimethylethylenediamine and N,N'-dimethyl-1,6-diminohexane as well as the diamines of the formula $H_2N(CH_2)_3O(CH_2)_2O(CH_2)_3NH_2$ and $N_2N(CH_2)_3S(CH_2)_2S(CH_2)_3NH_2$ and similar polyethylene oxide or polydithioethylene diamines; carbocyclic aliphatic diamines such as, but not limited to, 1,2-diaminocyclohexane, 1,3-diaminocyclohexane, 1,4-diaminocyclohexane, 1,3-diaminecyclopentane, 1,4-diaminocycloheptane, and other similar cycli aliphatic diamines; carbocyclic aromatic diamines such as, but not limited to, o-phenylenediamine, m-phenylenediamine, p-phenylenediamine, diaminotoluenes, 2,4-diaminotoluene, 1,4-diamino-2-methoxybenzene, 2,5-diaminoxylene, 1,3-diamino-4-chlorobenzene, 4,4'-diaminodiphenylmethane, 4,4'diaminodiphenyl ether, 4,4'-diaminodiphenyl thioether, 4,4'-diaminodiphenylsulphone, 2,2'-diaminobenzophenone, 4,4'-diaminodiphenylurea, 1,8-diaminonaphthalene, 1,5-diaminonaphthalene, benzidine, 3,3'-dimethyoxybenzidine, 2,2'-bis-(trifluoromethyl)benzidine, 2,2'-dimethylbenzidine, 2,2'-dichlorobenzidine, and other similarly substituted benzidines, 1,4-bis(2-methyl-4 TM aminopentyl)-benzene and 1,4-bis-(aminomethyl)-benzene; heterocyclic diamines such as, but not limited to, 2,6-diaminopyridine, 2,4-diaminopyrimidine, 2,4-diamino-s-triazine and other similar heterocyclic diamines.

The polycondensation reaction of the compounds of the formula (I) with one or more compounds of the formula (IV) and, optionally, one or more compounds of the formula (V) is carried out in a manner which is in itself known, appropriately at temperatures of about $-50$ C to $+300$ C. The reaction can be carried out in the melt or, preferably, in an inert organic solvent or a solvent mixture. Temperatures of $-20$ C to $+50$ C are preferred for the polycondensation reaction in solution.

Examples of suitable organic solvents are: chlorinated aromatic hydrocarbons, such as chlorobenzene and dichlorobenzenes, chlorinated aliphatic hydrocarbons, such as methylene chloride, chloroform, tetrachloroethane and tetrachloroethylene, aliphatic and cycloaliphatic ketones, such as acetone, methyl ethyl ketone, cyclopentanone and cyclohexanone, cyclic ethers, such as tetrahydrofurane, tetrahydropyrane and dioxane, cyclic aides, such as N-methyl-2-pyrrolidone, N-acetyl-2-pyrrolidone and N-methyl-a-caprolactam, N,N-dialkylaides of aliphatic monocarboxylic acids with 1-3 carbon atoms in the acid part, such as N,N-dimethylformamide, N,N-dimethylacetamide, N,N-diethylacetamide and N,N-dimethylmethoxyacetamide, hexamethylphosphoric acid triamide (hexametapol), N,N,N',N'-tetramethylurea, tetrahydrothiophene dioxide (sulpholane) and dialkylsulphoxides, such as dimethylsulphoxide and diethylsulphoxide.

Preferred solvents are N,N-dialkylamides of aliphatic monocarboxylic acids with 1-3 carbon atoms in the acid part, especially N,N-dimethylacetamide, as well as cyclic amides, such as N-methyl-2-pyrrodone.

The hydrochloric acid obtained during the condensation reaction with compounds of the formula (IV) in which Y represents chlorine can be removed by neutralization with basic substances, such as calcium hydroxide or triethylamine, or by reaction with an epoxide compound, such as ethylene oxide or propylene oxide, and by washing out with suitable solvents.

The condensation reactions are appropriately carried out with the exclusion of moisture, for example in an inert gas atmosphere, such as nitrogen.

As already mentioned initially, the reaction of the di-tri- or tetra-carboxylic acid derivatives of the formula (IV) with the diamines of the formula (I) and/or (V) can also be carried out stepwise in order to manufacture polymers which, at least in part, have a block-type distribution of repeat units of the formula (VI) and repeat units of formula (VII). It is also possible to link polyamides, polyamide-amide-acids or polyamide-acids which have 1 to 100 mole percent of repeat units of formulas (VI) and 99 to 0 mole percent of repeat units of formula (V) and have been manufactured separately, with one another and so-called block copolymers are formed by this means. In all of these cases, the reaction is carried out in a manner which is in itself known using a slight excess of one or the other reactant in order to obtain prepolymers which have end groups suitable for the further reaction, for example amino end groups, acid chloride groups and/or anhydride groups.

The optional cyclization of the polyamide-acids or polyamide-amide-acids ($k$ is equal to 3 and $n$ or $m$ is equal to 1 or $k$ is equal to 4 and both $n$ or $m$ are equal to 1) obtained after the condensation reaction is carried out in a manner which is in itself known by chemical means or by means of heat.

The chemical cyclization is appropriately carried out by treatment with a dehydrating agent on its own or as a mixture with a tertiary amine. Reagents which can be used are, for example, acetic anhydride, propionic anhydride and dicyclohexylcarbodimide or mixtures of acetic anhydride and triethylamine.

The cyclization by means of heat is carried out by heating to temperatures of about 50° C. to 300° C. and preferably of about 150° C. to 250° C. and optionally with the addition of an inert organic solvent.

The polyamides, polyamide-amide-acids and polyamide-acids according to the invention, as well as the corresponding cyclized derivatives, are suitable for the manufacture of shaped articles of very diverse types, such as fibers, films, sheets, coating compositions, foams, laminating resins, composite materials, molding powders, pressed articles and the like, in a manner which is in itself known, if desired with the use of customary additives, such as pigments, fillers and the like. The polymers according to the invention can also be processed easily from the melt and are distinguished by good mechanical, electrical and thermal properties as well as, in general, by good solubility in organic solvents, such as N,N-dimethyl acetamide, N,N-dimethylformamide and N-methyl-2-pyrrolidone.

BEST MODE FOR CARRYING OUT THE INVENTION

Applicants have found that the polyamides, polyamide-amide-acids and polyamide-acids, as well as the corresponding cyclized derivatives of polyamide-amide-acids, polyamide-imides, and polyamide-acids, polyimides, derived from diamines of formula (I) or copolymer having at least 1 mole percent polymer derived from diamines of formula (I) represent a new and novel class of soluble high performance polymers. When rigid, aromatic polycarboxy compounds of formula (IV) are used in the manufacture of polyamides, polyamide-imides and polyimides, these preferred polymers of the present invention represent a novel class of soluble and rigid-rod high performance polymers which maintain standard polyamides, polyamide-imides and polyimides properties such as outstanding modulus, tensile and compression strength, energy absorption, coefficient of expansion and electrical properties. The fact that these polymers have good solubility and can be manufactured with rigid structures makes them ideally suited for use in the production of antiballistics, reinforced molecular composites, microelectronic coatings and membranes because the polymers can be solution cast or deposited.

In preparing the homopolyamide, a near one to one mixture of a diamines of formula (I) such as 1,4-bis[4-aminophenyl]-2,3,5-triphenylbenzene (Ia) and a polycarboxylated compound of formula (IV) such as dichloro-teraphthalic acid (XII)

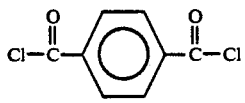

(XII)

are allowed to react under the above stated reaction conditions to from a polyamide of the following repeat formula (XIII)

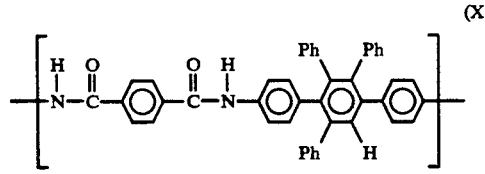

(XIII)

In preparing the homopolyamide-amide-acids, a near one to one mixture of a diamine of formula (I) such as 1,4-bis[4-aminophenyl]-2,3,5-triphenylbenzene (Ia) and a polycarboxylated compound of formula (XI) such as trimellitic acid (XV)

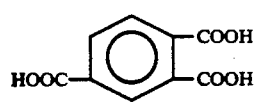

(XV)

are allowed to react under the above stated reaction conditions to from a polyamide-amide-acid of the following repeat formula (XVI)

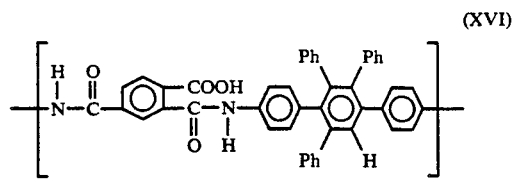

(XVI)

The polymers of repeat unit of formula (XVI) can be cyclized to polyamide-imides by standard techniques well known in the literature.

In preparing the homopolymaide-acid, a near one to one mixture of a diamine of formula (I) such as 1,4-bis[4-aminophenyl]-2,3,5-triphenylbenzene (Ia) and a polycarboxylated compound of formula (XI) such as pyromellitic acid (XVII)

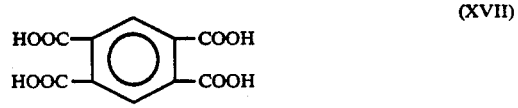

(XVII)

are allowed to react under the above stated reaction conditions to from a polyamide-acid of the following repeat formula (XVIII)

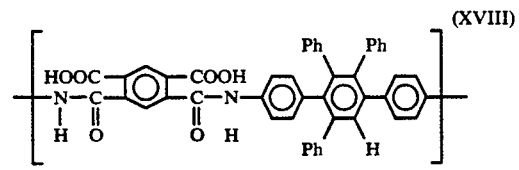

(XVIII)

The polymers of repeat unit of formula (XVIII) can be cyclized to polyamide-imides by standard techniques well known in the literature.

In preparing the copolymer consisting of 1 to 100 mole percent of repeat units of formula (IV) and 99 to 0 mole percent of repeat units of formula (V) it is understood that given molar amount of a combination of one or more diamines of formula (I) and one or more diamines of formula (XI) is mixed with a nearly equal molar amount of one or more polycarboxylated compound of formula (XI). This type of reaction mixture can be used to make copolyamides, copolyamide-amide-acids, copolyamide-imides, the cyclized version of cyclizable copolyamide-amide-acids, copolyamide-acids, and copolyimides, the cyclized version of cyclizable copolyamide-acids. The cyclization reaction can be done thermally or chemically with the preferred method utilizing the chemical additive isoquinoline in amount between about 0.1% and 5% by weight of solvent.

The diamines of the formula (I) in which both amino groups (NH2) are in the same position of the outer benzene rings, and in particular the diamines of the formula (I) in which both amino groups are in the para-position of the outer benzene rings is preferred.

Co-polyamides, co-polyamide-amide-acids and co-polyamide-acids having 10–90 mole percent of repeat units of formula (VI) and 90–10 mole percent of repeat units of formula (VII) are particularly preferred. These copolymers are preferred because they allow the expression of properties of the diamines of formula (I) and minimize the increased cost of using diamines of formula (I) in copolymers of the present invention.

In all the above polymers indicated by 1 to 100 mole percent of repeat units of formula (IV) and 99 to 0 mole percent of repeat units of formula (V), the end groups of the polymers can be either an acid, an amine, an anhydride or a combination of any of these groups. The reaction can also be carried out in the presence of a chain limiting reagent such as a mono function carboxylic acid or a mono functional amine containing organic reagent. These chain limiting reagents actually stop polymerization by introducing a non-reactive group at the end of a polymer chain. In the case of carboxylic acid chain limiting reagents, the reagent can be selected from the representative and illustrative group consisting of benzoic acid, naphthoic acid, or alkyl substituted benzoic acids. In the case of organic amine chain limiting reagents, the reagent can be selected from the group consisting of aniline, alkyl substituted anilines, or naphthyl amines.

The invention will be better understood by reference to the following examples which are included for purposes of illustration and not limitation.

PREPARATION OF DINITRO INTERMEDIATE OF FORMULA (I)

EXAMPLE 1

This example illustrates the preparation of 1,4-bis(4-nitrophenyl)-2,3,5-triphenylbenzene, a dinitro intermediate of formula (1), where $Ar_1$, $Ar_2$, and $Ar_3$ are phenyl and $R_1$ is hydrogen.

1,4-bis(4-nitrophenyl)-2,3,5-triphenylbenzene was prepared according to the procedure described in L. F., "Organic Experiments", 2nd Ed., 297 (1968). 19.3 grams (0.189 moles) of phenylacetylene, 20.0 grams (0.0362 moles) of 2,5-bis(4-nitrophenyl)-3,4-diphenylcyclopentadienone, a compound of formula (II) where $Ar_1$ and $Ar_2$ are phenyl, and 130 mL of o-dichlorobenzene were stirred at 180° C. for 2 hours. The reaction mixture was cooled, poured into 500 mL of hexane and filtered. The reaction yielded 22.9 grams of 1,4-bis(4-nitrophenyl)-2,3,5-triphenylbenzene, a 66% yield.

EXAMPLE 2

This example illustrates the preparation of 1,4-bis(4-nitrophenyl)-2,3,5,6-tetraphenylbenzene, a dinitro intermediate of formula (I), where $Ar_1$, $Ar_2$, and $Ar_3$ are phenyl and $R_1$ is phenyl.

1,4-bis(4-nitrophenyl)-2,3,5,6-tetraphenylbenzene was prepared according to the same procedure as described in Example 1 with diphenylacetylene being use in place of phenylacetylene. The reaction time had to be increased to 17 hrs to complete the cycloaddition reaction and a yield of 63% was attained.

PREPARATION OF DIAMINES OF FORMULA (I)

EXAMPLE 3

This example illustrates the preparation of 1,4-bis(4-aminophenyl)-2,3,5-triphenylbenzene, a dinitro intermediate of formula (1), where $Ar_1$, $Ar_2$, and $Ar_3$ are phenyl and $R_1$ is hydrogen.

Under heating, 20.0 grams (0.0365 moles) of 1,4-bis(4-aminophenyl)-2,3,5-triphenylbenzene was stirred with 250 mL of 2-methoxyethanol. When the temperature was raised to 80° C., a solution of 82.2 grams (0.364 moles) of stannous chloride in 13o mL of hydrochloric acid was added. Thereafter, the mixture was stirred around 100° C. for 5 hours. After cooling, the mixture was poured into 600 mL of water and filtered. The solid obtained was neutralized by ammonium hydroxide, washed with water and dried. The yield was 10 0 grams (61%). The crude product was recrystallized from toluene.

The properties of 1,4-bis(4-aminophenyl)-2,3,5-triphenylbenzene were: mp=256°-258° C.; IR (KBr) 3460 and 3480 $cm_{-1}$ ($NH_2$); $^1$H-NMR ($CDCl_3$) $\delta=3.3$ (s, 4H, $NH_2$), 6.0-7.3 (m, 24H, aromatic H); Anal. Calcd. for $C_{36}H_{28}N_2$: C, 88.49, H, 5.78, N, 5.73; Found: C, 88.85, H, 5.83, N, 5.58.

EXAMPLE 4

This example illustrates the preparation of 1,4-bis(4-aminophenyl)-2,3,5,6-tetraphenylbenzene, a dinitro intermediate of formula (1), where $Ar_1$, $Ar_2$, and $Ar_3$ are phenyl and $R_1$ is phenyl.

1,4-bis(4-aminophenyl)-2,3,5,6-tetraphenylbenzene was prepared according to the procedure set forth in Example 2 with 1,4-bis(4-nitrophenyl)-2,3,5,6-tetraphenylbenzene being used at the same molar amount as 1,4-bis(4-nitrophenyl)-2,3,5-triphenylbenzene in Example 3, but the yield was only 45%. The crude product was recrystallized from pyridine.

The properties of 1,4-bis(4-aminophenyl)-2,3,5,6-tetraphenylbenzene were: mp=453° C. (DSC); IR (KBr) 3380 and 3450 $cm_{-1}$ ($NH_2$); Anal. Calcd. for $C_{42}H_{32}N_2$: C, 89.33, H, 5.71, N, 4.96: Found: C, 88.54, H, 5.64, N, 4.92.

In the next set of examples, $T_{-5\%}$ means the temperature at which a 5% weight loss is detected.

PREPARATION OF A HOMOPOLYAMIDE

EXAMPLE 5

This example illustrates the preparation of a polyamide consisting of 100 mole percent of repeat unit of formula (VI) where the diamine of formula (I) represents the diamine prepared in example 2, 1,4-bis(4-aminophenyl)-2,3,5-triphenylbenzene, and the polycarboxy compound of formula (IV) is terephthoyl chloride.

0.4 grams (0.0008186 mole) of 1,4-bis(4-aminophenyl)-2,3,5-triphenylbenzene, synthesized according to example 2, was dissolved in 2.9 grams of NMP, cooled in an ice bath to below 5° C and kept under an inert atmosphere such as nitrogen during the course of the polymerization. 0.1662 grams (0.0008186 mole) of terephthoyl chloride (TPC) was added to the solution and stirred for 30 minutes. This represented a 6% concentrated solution of starting material in solvent. The ice bath was removed shortly after TPC addition. The mixture became viscous and turned brown-yellow transparent color. After approximately 15 hours, the mixture was poured into 500 mL of methanol to affect coagulation. The polymer was filtered, dried and the yield was 97%.

Polymer properties: $[\eta]_{inh}=2.87$ dL/g in NMP at 30° C.; $T_{-5\%}=508°$ C. in nitrogen; $T_{-5\%}=493°$ C. in air; soluble in NMP at room temperature; tough transparent film.

It should be appreciated that any other polycarboxy compound of formula (IV) can be substituted into the above synthesis to yield an analogous polymer.

EXAMPLE 6

This example illustrates the preparation of a polyamide consisting of 100 mole percent of repeat unit of formula (VI) where the diamine of formula (I) represents the diamine prepared in example 2, 1,4-bis(4-aminophenyl)-2,3,5-triphenylbenzene, and the polycarboxy compound of formula (IV) is terephthoyl chloride.

This polyamide was prepared according to Example 5 except the starting material concentration was 14%. The polymer solution Was transparent.

Polymer properties: $[\eta]_{inh}=2.99$ dL/g in NMP at 30° C.; $T_{-5\%}=508°$ C. in nitrogen; $T_{-5\%}=493°$ C. in air; soluble in NMP at room temperature; tough transparent film.

EXAMPLE 7

This example illustrates the preparation of a polyamide consisting of 100 mole percent of repeat unit of formula (VI) where the diamine of formula (I) represents the diamine prepared in example 2, 1,4-bis(4-aminophenyl)-2,3,5-triphenylbenzene, and the polycarboxy compound of formula (IV) is isophthoyl chloride.

This polyamide was prepared according to Example 5 except isophthoyl chloride was used instead of its isomeric analog terephthoyl chloride and the starting material concentration was 14%. The polymer solution was transparent.

Polymer properties: $[\eta]_{inh}=0.88$ dL/g in NMP at 30° C.; $T_{-5\%}=509°$ C. in nitrogen; $T_{-5\%}=520°$ C. in air; soluble in NMP at room temperature; tough transparent film.

EXAMPLE 8

This example illustrates the preparation of a polyamide consisting of 100 mole percent of repeat unit of formula (VI) where the diamine of formula (I) represents the diamine prepared in example 2, 1,4-bis(4-aminophenyl)-2,3,5,6-tetraphenylbenzene, and the polycarboxy compound of formula (IV) is terephthoyl chloride.

This polyamide was prepared according to Example 5 except 1,4-bis(4-aminophenyl)-2,3,5,6-tetraphenylbenzene was used instead of 1,4-bis(4-aminophenyl)-2,3,5-triphenylbenzene and the starting material concentration was 8%. The polymer precipitated and the yield was 78%.

Polymer properties: $[\eta]_{inh}=0.46$ dL/g in sulfuric acid at 30° C.; $T_{-5\%}=516°$ C. in nitrogen; $T_{-5\%}=524°$ C. in air.

EXAMPLE 9

This example illustrates the preparation of a polyamide consisting of 100 mole percent of repeat unit of formula (VI) where the diamine of formula (I) represents the diamine prepared in example 2,1,4-bis(4-aminophenyl)-2,3,5,6-tetraphenylbenzene, and the polycarboxy compound of formula (IV) is terephthoyl chloride.

This polyamide was prepared according to Example 5 except 1,4-bis(4-aminophenyl)-2,3,5,6-tetraphenylbenzene was used instead of 1,4-bis(4-aminophenyl)-2,3,5-triphenylbenzene, a two molar amount of lithium chloride based on the moles of diamine was added to the reaction after the monomer addition and the starting material concentration was 14%. The polymer solution was cloudy and the yield was 83%.

Polymer properties: $[\eta]_{inh}=0.93$ dL/g in sulfuric acid at 30° C.; $T_{-5\%}=516°$ C. in nitrogen; $T_{-5\%}=524°$ C. in air.

EXAMPLE 10

This example illustrates the preparation of a polyamide consisting of 100 mole percent of repeat unit of formula (VI) where the diamine of formula (I) represents the diamine prepared in example 2, 1,4-bis(4-aminophenyl)-2,3,5,6-tetraphenylbenzene, and the polycarboxy compound of formula (IV) is isophthoyl chloride.

This polyamide was prepared according to Example 5 except 1,4-bis(4-aminophenyl)-2,3,5,6-tetraphenylbenzene was used instead of 1,4-bis(4-aminophenyl)-2,3,5-triphenylbenzene, isophthoyl chloride was used instead of terephthoyl chloride and the starting material concentration was 14%. The polymer precipitated and the yield was 91%.

Polymer properties: $[\eta]_{inh}=0.49$ dL/g in sulfuric acid at 30° C.; $T_{-5\%}=514°$ C. in nitrogen; $T_{-5\%}=516°$ C. in air; a tough film was cast from sulfuric acid.

EXAMPLE 11

This example illustrates the preparation of a polyamide consisting of 100 mole percent of repeat unit of formula (VI) where the diamine of formula (I) represents the diamine prepared in example 2, I,4-bis(4-aminophenyl)-2,3,5,6-tetraphenylbenzene, and the polycarboxy compound of formula (IV) is isophthoyl chloride.

This polyamide was prepared according to Example 5 except 1,4-bis(4-aminophenyl)-2,3,5,6-tetraphenylbenzene was used instead of 1,4-bis(4-aminophenyl)-2,3,5-triphenylbenzene, isophthoyl chloride was used instead of terephthoyl chloride, a two molar amount of lithium chloride based on the moles of diamine was added to the reaction after the monomer addition and the starting material concentration was 15%. The polymer solution was cloudy and the yield was 81%.

Polymer properties: $[\eta]_{inh}=0.46$ dL/g in sulfuric acid at 30° C.; $T_{-5\%}=514°$ C. in nitrogen; $T_{-5\%}=516°$ C. in air; a tough film was cast from sulfuric acid.

EXAMPLE 12

This example illustrates the preparation of a polyimide consisting of 100 mole percent of repeat unit of formula (VI) where the diamine of formula (I) represents the diamine prepared in example 2, 1,4-bis(4-aminophenyl)-2,3,5-triphenylbenzene, and the polycarboxy compound of formula (IV) is pyromellitic dianhydride.

0.35 grams (0.0007163 mole) of 1,4-bis(4-aminophenyl)-2,3,5-triphenylbenzene, synthesized according to example 2, was dissolved in 9.0 grams of m-cresol under nitrogen. 0.1562 grams of pyromellitic dianhydride (PMDA) (0.0007161 mole) was added to the solution along with 3 ml of toluene and 3 drops of isoquinoline. (Isoquinoline is an optional ingredient which promotes the cyclization reaction.) This solution represented a 5% concentration of starting material in solvent. The reaction was heated to 170° C. The toluene is added to azeotrope of the water formed during the reaction. When the distillation of toluene was over, 3 mL of fresh toluene was added. This operation was repeated three times to insure complete removal of the water of reaction. The temperature was then maintained at 190° C for 3 hours. After a couple of hours, an aliquot of the polymer mixture was cast into a film. After cooling, the reaction mixture was poured in to 500 mL of methanol to affect coagulation. The product obtained was washed with methanol and dried. The polymer was filtered and the yield was 94%.

Polymer properties: $[\eta]_{inh}=3.16$ dL/g in sulfuric acid at 30° C.; $T_{-5\%}=583°$ C. in nitrogen; $T_{-5\%}=546°$ C. in air; insoluble in CHCl$_3$ and NMP at room temperature.

It should be appreciated that any other polycarboxy compound of formula (IV) can be substituted into the above synthesis to yield an analogous polymer.

EXAMPLE 13

This example illustrates the preparation of a polyimide consisting of 100 mole percent of repeat unit of formula (VI) where the diamine of formula (I) represents the diamine prepared in example 2, 1,4-bis(4-aminophenyl)-2,3,5-triphenylbenzene, and the polycarboxy compound of formula (IV) is pyromellitic dianhydride.

The polyimide was prepared according to Example 12 except the concentration of starting material in solvent was 15%. The solution was gelatinous and not homogeneous as in Example 12.

Polymer properties: $[\eta]_{inh}=3.16$ dL/g in sulfuric acid at 30° C.; $T_{-5\%}=583°$ C. in nitrogen; $T_{-5\%}=546°$ C. in air; insoluble in CHCl$_3$ and NMP at room temperature.

It should be appreciated that any other polycarboxy compound of formula (IV) can be substituted into the above synthesis to yield an analogous polymer.

EXAMPLE 14

This example illustrates the preparation of a polyimide consisting of 100 mole percent of repeat unit of formula (VI) where the diamine of formula (I) represents the diamine prepared in example 2, 1,4-bis(4-aminophenyl)-2,3,5-triphenylbenzene, and the polycarboxy compound of formula (IV) is 3,3',4,4'-diphenyl-tetracarboxylic acid dianhydride.

The polyimide was prepared according to Example 12 except 3,3',4,4'-diphenyl-tetracarboxylic acid dianhydride was used instead of PMDA and the concentration of starting material in solvent was 7%. The yield of product was 92%.

Polymer properties: $[\theta]_{inh}=1.89$ dL/g in NMP at 30° C.; $T_{-5\%}=601°$ C. in nitrogen; $T_{-5\%}=564°$ C. in air; soluble in CHCl$_3$ and NMP at room temperature; a tough film was cast from NMP.

EXAMPLE 15

This example illustrates the preparation of a polyimide consisting of 100 mole percent of repeat unit of formula (VI) where the diamine of formula (I) represents the diamine prepared in example 2,1,4-bis(4-aminophenyl)-2,3,5-triphenylbenzene, and the polycarboxy compound of formula (IV) is bis(3,4-dicarboxyphenyl) ether dianhydride.

The polyimide was prepared according to Example 12 except bis(3,4-dicarboxyphenyl) ether dianhydride was used instead of PMDA and the concentration of starting material in solvent was 7%. The yield of product was 94%.

Polymer properties: $[\eta]_{inh}=0.83$ dL/g in sulfuric acid at 30° C.; $T_{-5\%}=576°$ C. in nitrogen; $T_{-5\%}=539°$ C. in air; soluble in CHCl$_3$ and NMP at room temperature; a tough film was cast from NMP.

EXAMPLE 16

This example illustrates the preparation of a polyimide consisting of 100 mole percent of repeat unit of formula (VI) where the diamine of formula (I) represents the diamine prepared in example 2, 1,4-bis(4-aminophenyl)-2,3,5-triphenylbenzene, and the polycarboxy compound of formula (IV) is bis-(3,4-dicarboxyphenyl)-sulphone dianhydride.

The polyimide was prepared according to Example 12 except bis-(3,4-dicarboxyphenyl)-sulphone dianhydride was used instead of PMDA and the concentration of starting material in solvent was 7%. The yield of product was 90%.

Polymer properties: $[\eta]_{inh}=0.66$ dL/g in sulfuric acid at 30° C.; $T_{-5\%}=504°$ C. in nitrogen; $T_{-5\%}=524°$ C. in air; insoluble in CHCl$_3$ and NMP at room temperature; a tough film was cast from NMP.

EXAMPLE 17

This example illustrates the preparation of a polyimide consisting of 100 mole percent of repeat unit of formula (VI) where the diamine of formula (I) represents the diamine prepared in example 2, 1,4-bis(4-aminophenyl)-2,3,5,6-tetraphenylbenzene, and the polycarboxy compound of formula (IV) is pyromellitic dianhydride.

The polyimide was prepared according to Example 12 except 1,4-bis(4-aminophenyl)-2,3,5,6-tetraphenylbenzene was used instead of 1,4-bis(4-aminophenyl)-2,3,5-triphenylbenzene and the concentration of starting material in solvent was 7%. The yield was 97%.

Polymer properties: $[\eta]_{inh}=1.14$ dL/g in sulfuric acid at 30° C.; $T_{-5\%}=572°$ C. in nitrogen; $T_{-5\%}=473°$ C. in air; insoluble in CHCl: and NMP at room temperature.

It should be appreciated that any other polycarboxy compound of formula (IV) can be substituted into the above synthesis to yield an analogous polymer.

EXAMPLE 18

This example illustrates the preparation of a polyimide consisting of 100 mole percent of repeat unit of formula (VI) where the diamine of formula (I) represents the diamine prepared in example 2, 1,4-bis(4-aminophenyl)-2,3,5,6-tetraphenylbenzene, and the polycarboxy compound of formula (IV) is 3,3',4,4'-diphenyl-tetracarboxylic acid dianhydride.

The polyimide was prepared according to Example 12 except 1,4-bis(4-aminophenyl)-2,3,5,6-tetraphenylbenzene was used instead of 1,4-bis(4-aminophenyl)-2,3,5-triphenylbenzene, 3,3',4,4'-diphenyl-tetracarboxylic acid dianhydride was used instead of PMDA and the concentration of starting material in solvent was 10%. The yield of product was 99%.

Polymer properties: $[\eta]_{inh}=1.54$ dL/g in sulfuric acid at 30° C.; $T_{-5\%}=580°$ C. in nitrogen; $T_{-5\%}=557°$ C. in air; partially soluble in CHCl$_3$ and NMP at room temperature; a tough film was cast from NMP.

EXAMPLE 19

This example illustrates the preparation of a polyimide consisting of 100 mole percent of repeat unit of formula (VI) where the diamine of formula (I) represents the diamine prepared in example 2,1,4-bis(4-aminophenyl)-2,3,5,6-tetraphenylbenzene, and the polycarboxy compound of formula (IV) is bis(3,4-dicarboxyphenyl) ether dianhydride.

The polyimide was prepared according to Example 12 except 1,4-bis(4-aminophenyl)-2,3,5,6-tetraphenylbenzene was used instead of 1,4-bis(4-aminophenyl)-2,3,5-triphenylbenzene, bis(3,4-dicarboxyphenyl) ether dianhydride was used instead of PMDA and the concentration of starting material in solvent was 9%. The yield of product was 95%.

Polymer properties: $[\eta_{inh}=0.61$ dL/g in sulfuric acid at 30° C.; $T_{-5\%}=571°$ C. in nitrogen; $T_{-5\%}=523°$ C. in air; partially soluble in NMP at room temperature; a tough film was cast from NMP.

EXAMPLE 20

This example illustrates the preparation of a polyimide consisting of 100 mole percent of repeat unit of formula (VI) where the diamine of formula (I) represents the diamine prepared in example 2, 1,4-bis(4-aminophenyl)-2,3,5,6-tetraphenylbenzene, and the polycarboxy compound of formula (IV) is bis-(3,4-dicarboxyphenyl)-sulphone dianhydride.

The polyimide was prepared according to Example 12 except 1,4-bis(4-aminophenyl)-2,3,5,6-tetraphenylbenzene was used instead of 1,4-bis(4-aminophenyl)-2,3,5-triphenylbenzene, bis-(3,4-dicarboxyphenyl)-sulphone dianhydride was used instead of PMDA and the concentration of starting material in solvent was 7%. The yield of product was 94%.

Polymer properties: $[\eta]_{inh}=0.67$ dL/g in sulfuric acid at 30° C.; $T_{-5\%}=527°$ C. in nitrogen; $T_{-5\%}=535°$ C. in air; soluble NMP at room temperature; a tough film was cast from NMP.

PREPARATION OF A COPOLYMERS

EXAMPLE 21

This example illustrates the preparation of a copolyamide consisting of 50 mole percent of repeat unit of formula (VI) where the diamine of formula (I) represents the diamine prepared in example 2, 1,4-bis(4-aminophenyl)-2,3,5-triphenylbenzene, and the polycarboxy compound of formula (IV) is terephthoyl chloride and 50 mole percent of repeat unit of formula (VII) where the diamine of formula (V) is 4,4'-diaminodiphenyl ether and the polycarboxy compound of formula (IV) is terephthoyl chloride.

0.4 grams (0.0008186 mole) of 1,4-bis(4-aminophenyl)-2,3,5-triphenylbenzene, synthesized according to example 2, and 0.1637 grams (0.0008186 moles) of 4,4'-diaminodiphenyl ether is dissolved in 12 ml NMP, cooled in an ice bath and kept under an inert atmosphere such as nitrogen during the course of the polymerization. 0.2324 grams (0.0016372 moles) of terephthoyl chloride (TPC) is added to the solution along with 4 ml of NMP. The ice bath is removed shortly after TPC addition. The mixture becomes viscous and turned brown-yellow transparent color. After approximately 10 hours, the mixture is diluted in approximately 40 ml of NMP and poured into 1 liter of methanol to affect coagulation. The polymer is filtered and the yield was 97%.

It should be appreciated that any other diamine of formula (V) or any other polycarboxy compound of formula (IV) can be substituted into the above synthesis to yield an analogous polymer.

EXAMPLE 22

This example illustrates the preparation of a mixed copolyamide consisting of 50 mole percent of repeat unit of formula (VI) where the diamine of formula (I) represents the diamine prepared in example 2, 1,4-bis(4-aminophenyl)-2,3,5-triphenylbenzene, and two polycarboxy compound of formula (IV), terephthoyl chloride and isophthoyl chloride, and 50 mole percent of repeat unit of formula (VII) where the diamine of formula (V) is 4,4'-diaminodiphenyl ether and two polycarboxy compound of formula (IV), terephthoyl chloride and isophthoyl chloride.

0.4 grams (0.0008186 mole) of 1,4-bis(4-aminophenyl)-2,3,5-triphenylbenzene, synthesized according to example 2, and 0.164 grams (0.0008186 moles) of 4,4'-diaminodiphenyl ether is dissolved in 12 ml NMP, cooled in an ice bath and kept under an inert atmosphere such as nitrogen during the course of the polymerization. 0.1662 grams (0.0008186 moles) of terephthoyl chloride (TPC) and 0.1662 grams (0.0008186 moles) of isophthoyl chloride (IPC) is added to the solution along with 4 ml of NMP. The ice bath is removed shortly after TPC and IPC addition. The mixture becomes viscous and turned brown-yellow transparent color. After approximately 10 hours, the mixture is diluted in approximately 40 ml of NMP and poured into 1 liter of methanol to affect coagulation. The polymer is filtered and the yield was 97%.

It should be appreciated that any other diamine of formula (V) or any other polycarboxy compound of formula (IV) can be substituted into the above synthesis to yield an analogous polymer.

EXAMPLE 23

This example illustrates the preparation of a polyamide-acid and the subsequent cyclization to the corresponding polyimide consisting of 50 mole percent of repeat unit of formula (VI) where the diamine of formula (I) represents the diamine prepared in example 2, 1,4-bis(4-aminophenyl)-2,3,5-triphenylbenzene, and the two polycarboxy compound of formula (IV) are pyromellitic dianhydride and bis-(3,4-dicarboxyphenyl) ether dianhydride and 50 mole percent of repeat unit of formula (VII) where the diamine of formula (V) is 4,4'-diaminodiphenyl ether and two polycarboxy compound of formula (IV) is pyromellitic dianhydride and bis-(3,4-dicarboxyphenyl) ether dianhydride 0.35 grams (0.0007163 mole) of 1,4-bis(4-aminophenyl)-2,3,5-triphenylbenzene, synthesized according to example 2, 0.1433 grams (0.0007163 moles) of 4,4'-diaminodiphenyl ether is dissolved in 11 ml m-cresol, cooled in an ice bath and kept under an inert atmosphere such as nitrogen during the course of the polymerization. 0.1562 grams of pyromellitic dianhydride (PMDA) (0.0007161 mole) and 0.2220 grams (0.0007161 moles) of bis-(3,4-dicarboxyphenyl) ether dianhydride is added to the solution along with 6 ml of toluene. The ice bath was removed shortly after PMDA addition and six drops of isoquinoline was added. The reaction was heated to dissolve PMDA. After a couple of hours, an aliquot of the polymer mixture was cast into a film. The mixture was diluted in approximately 40 ml of NMP and poured into 1 liter of methanol to affect coagulation. The polymer is filtered and the yield is about 91%.

It should be appreciated that any other diamine of formula (V) or any other polycarboxy compound of formula (IV) can be substituted into the above synthesis to yield an analogous polymer.

What is claimed is:

1. A polyamide, a polyamide-amide-acid or a polyamide-acid which comprises 1 to 100 mole percent of structural elements of the formula (VI)

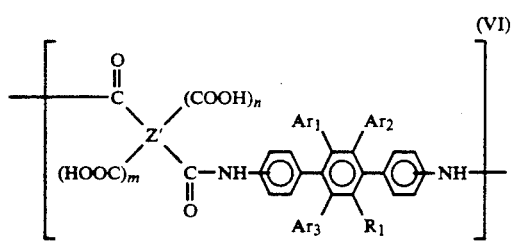

and from 99 to 0 mole percent of a repeat unit of formula (VII)

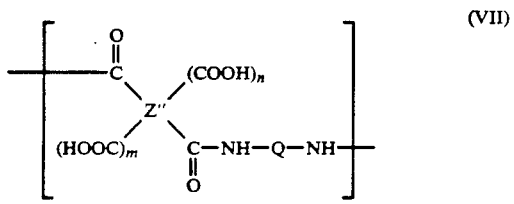

where both imido (CONH) groups are independently in either the meta or para position with respect to the covalent bond to the center polysubstituted benzene ring, where $Ar_1$, $Ar_2$, and $Ar_3$ are separately and independently aryl groups selected from the group consisting of a phenyl group, a halogen substituted phenyl group, an alkoxy substituted phenyl group, a halo-alkyl substituted phenyl group, an alkyl substituted phenyl group, or an cycloalkyl substituted phenyl group, where $R_1$ is selected from the group consisting of a H atom, an alkyl group, cycloalkyl group or an aryl group, $n$ and $m$ are whole numbers separately and independently having the numeric value of either 0 or 1, Z' and Z" is separately and independently one or more organic radical selected from the group consisting of an aliphatic radical, a cyclo-aliphatic radical, a carbocyclic-aromatic radical, or a hetero-cyclic aromatic radical, and Q is one or more divalent organic radical selected from the group consisting of an aliphatic radical having at least 2 carbon atoms, a carbocyclic aliphatic radical, a carbocyclic aromatic radical, or a heterocyclic radical.

2. A polyamide according to claim 1, wherein said polyamide comprises 100 mole percent of repeat unit formula (VI) where $n$ and $m$ are equal to the numeric value of 0 and where Z' and Z" are separately and independently one or more divalent radical derived from a polycarboxy compound of formula (IV)

Z(COY)

(IV)

where Z is an organic radical selected from the group consisting of an aliphatic radical, a cyclo-aliphatic radical, a carbocyclic-aromatic radical, or a hetero-cyclic aromatic radical, where Y is a halogen atom, a hydroxy group, an unsubstituted or substituted phenoxy group or an alkoxy group preferably having from about 1 to 18 carbon atoms, and particularly preferred having from about 1 to 12 carbon atoms, where $k$ is a whole number having a numeric value of 2 and where each COY is bonded to a different atom of Z.

3. A polyamide according to claim 2, wherein said Q is one or more divalent aromatic radical derived from a diamine of formula (V)

$H_2N$—Q—$NH_2$ (V)

where Q is a divalent organic radical selected from the representative and illustrative group consisting of an aliphatic radical having at least 2 carbon atoms, a carbocyclic aliphatic radical, a carbocyclic aromatic radical, or a heterocyclic radical.

4. A polyamide-amide-acid according to claim 1, wherein said polyamide-amide-acid comprises 100 mole percent of repeat unit formula (VI) where either $n$ or $m$ is equal to the numeric value of 1, and where Z' and Z" are separately and independently one or more trivalent radical derived from a polycarboxy compound of formula (IV)

Z(COY)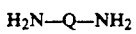

(IV)

where Z is an organic radical selected from the group consisting of an aliphatic radical, a cyclo-aliphatic radical, a carbocyclic-aromatic radical, or a hetero-cyclic aromatic radical, where Y is a halogen atom, a hydroxy group, an unsubstituted or substituted phenoxy group or an alkoxy group preferably having from about 1 to 18 carbon atoms, and particularly preferred having from about 1 to 12 carbon atoms, where $k$ is a whole number having a numeric value of 3 and where each COY is bonded to a different atom of Z and when $k$ is equal to 3 and Z is a cyclic organic radical, then two of the COY groups are in an ortho orientation relative to each other.

5. A polyamide-amide-acid according to claim 4, wherein said polyamide-amide-acid is cyclized to the corresponding polyamide-imide.

6. A polyamide-amide-acid according to claim 4, wherein said Q is one or more divalent aromatic radical derived from a diamine of formula (V)

$H_2N$—Q—$NH_2$ (V)

where Q is a divalent organic radical selected from the representative and illustrative group consisting of an aliphatic radical having at least 2 carbon atoms, a carbocyclic aliphatic radical, a carbocyclic aromatic radical, or a heterocyclic radical.

7. A polyamide-amide-acid according to claim 6, wherein said polyamide-amide-acid is cyclized to the corresponding polyamide-imide.

8. A polyamide-acid according to claim 1, wherein said polyamide-acid comprises 100 mole percent of repeat unit formula (VI) where both $n$ or $m$ are equal to the numeric value of 1, and where Z' and Z" are separately and independently one or more tetravalent radical derived from a polycarboxy compound of formula (IV)

Z(COY)

(IV)

where Z is an organic radical selected from the group consisting of an aliphatic radical, a cyclo-aliphatic radical, a carbocyclic-aromatic radical, or a hetero-cyclic aromatic radical, where Y is a halogen atom, a hydroxy group, an unsubstituted or substituted phenoxy group or an alkoxy group preferably having from about 1 to 18 carbon atoms, and particularly preferred having from about 1 to 12 carbon atoms, where $k$ is a whole number having a numeric value of 4 and where each COY is bonded to a different atom of Z and when $k$ is equal to 4 and Z is a cyclic organic radical, then each pair of COY groups are arranged in an ortho orientation relative to one another.

9. A polyamide-acid according to claim 8, wherein said polyamide-acid is cyclized to the corresponding polyimide.

10. A polyamide-acid according to claim 8, wherein said Q is one or more divalent aromatic radical derived from a diamine of formula (V)

$$H_2N-Q-NH_2 \qquad (V)$$

where Q is a divalent organic radical selected from the representative and illustrative group consisting of an aliphatic radical having at least 2 carbon atoms, a carbocyclic aliphatic radical, a carbocyclic aromatic radical, or a heterocyclic radical.

11. A polyamide-acid according to claim 10, wherein said polyamide-acid is cyclized to the corresponding polyimide.

12. A polyamide, a polyamide-amide-acid or a polyamide-acid according to claim 1, where said polyamide, polyamide-amide-acid or polyamide-acid consisting of 10 to 90 mole percent of repeat units of formula (VI) and 10 to 90 mole percent of repeat units of formula (VII).

13. A polyamide, polyamide-amide-acid, or polyamide-acid according to claim 12, wherein either $n$ or $m$ is equal to the numeric value of 1, and where Z' and Z" are separately and independently one or more polyvalent radical derived from a polycarboxy compound of formula (IV)

$$Z(COY)_k \qquad (IV)$$

where Z is an organic radical selected from the group consisting of an aliphatic radical, a cyclo-aliphatic radical, a carbocyclic-aromatic radical, or a hetero-cyclic aromatic radical, where Y is a halogen atom, a hydroxy group, an unsubstituted or substituted phenoxy group or an alkoxy group preferably having from about 1 to 18 carbon atoms, and particularly preferred having from about 1 to 12 carbon atoms, where $k$ is a whole number having a numeric value of 2, 3 or 4 and where each COY is bonded to a different atom of Z and when $k$ is equal to 3 and Z is a cyclic organic radical, then two of the COY groups are in an ortho orientation relative to each other and when $k$ is equal to 4 and Z is a cyclic organic radical, then each pair of COY groups are arranged in an ortho orientation relative to one another and said Q is one or more divalent aromatic radical derived from a diamine of formula (V)

$$H_2N-Q-NH_2 \qquad (V)$$

where Q is a divalent organic radical selected from the representative and illustrative group consisting of an aliphatic radical having at least 2 carbon atoms, a carbocyclic aliphatic radical, a carbocyclic aromatic radical, or a heterocyclic radical.

14. A polyamide-amide-acid or polyamide-acid according to claim 13, wherein said polyamide-amide-acid or polyamide-acid is cyclized to the corresponding polyamide-imide or polyimide.

15. The polyamide, a polyamide-acid polymer of claim 1 wherein the polymer is soluble, melt processable and has a heat stability in air as measured by $T_{-5\%}$ in air of 493° C. and higher and exists as a rod-shaped polymer. Darms is devoid of a teaching to a rod-shaped polymer.

* * * * *